(12) United States Patent
Klass

(10) Patent No.: US 8,937,657 B2
(45) Date of Patent: Jan. 20, 2015

(54) PORTABLE THREE-DIMENSIONAL METROLOGY WITH DATA DISPLAYED ON THE MEASURED SURFACE

(76) Inventor: Erik Klass, Daisendorf (DE)

( * ) Notice: Subject to any disclaimer, the term of this patent is extended or adjusted under 35 U.S.C. 154(b) by 432 days.

(21) Appl. No.: 13/549,494

(22) Filed: Jul. 15, 2012

(65) Prior Publication Data

US 2014/0015963 A1 Jan. 16, 2014

(51) Int. Cl.
*H04N 7/18* (2006.01)
*G01B 11/00* (2006.01)
*G01B 11/03* (2006.01)
*G01B 11/04* (2006.01)

(52) U.S. Cl.
CPC ............... *G01B 11/00* (2013.01); *G01B 11/03* (2013.01); *G01B 11/04* (2013.01)
USPC ........................................................ 348/136

(58) Field of Classification Search
CPC ......... G01B 11/00; G01B 11/03; G01B 11/04
USPC ........................................................ 348/136
See application file for complete search history.

(56) References Cited

U.S. PATENT DOCUMENTS

| 7,570,370 | B2 | 8/2009 | Steinbichler et al. |
| 8,064,684 | B2 | 11/2011 | Ratti et al. |
| 2011/0019155 | A1 | 1/2011 | Daniel et al. |
| 2011/0173827 | A1 | 7/2011 | Bailey et al. |
| 2012/0057174 | A1 | 3/2012 | Briggs |

FOREIGN PATENT DOCUMENTS

WO   WO/2009/073009 A1   6/2009

OTHER PUBLICATIONS

Chai, L. et al., "3-D Motion and Structure Estimation Using Inertial Sensors and Computer Vision for Augmented Reality." Presence: Teleoperators and Virtual Environments v. 11, pp. 474-492 (MIT Press, 2000).
Glossop, N. * Wang, Z., "Laser projection augmented reality system for computer-assisted surgery." CARS 2003. Computer Assisted Radiology and Surgery. Proceedings of the 17th International Congress and Exhibition, International Congress Series v. 1256, pp. 65-71 (Elsevier Science B.V., Jun. 2003).

*Primary Examiner* — Allen Wong
(74) *Attorney, Agent, or Firm* — Elizabeth Anne Nevis; Rylander & Associates, PC; Philip R. M. Hunt

(57) ABSTRACT

A portable instrument for 3D surface metrology projects augmented-reality feedback directly on the measured target surface. The instrument generates structured-light measuring-patterns and projects them successively on a target surface. Features, contours, and textures of the target surface distort each projected measuring-pattern image (MPI) from the original measuring-pattern. The instrument photographs each MPI, extracts measurement data from the detected distortions, and derives a result-image from selected aspects of the measurement data. The instrument warps the result-image to compensate for distortions from the projector or surface and projects the result-image on the measured surface, optionally with other information such as summaries, instrument status, menus, and instructions. The instrument is lightweight and rugged. Accurate measurements with hand-held embodiments are made possible by high measurement speed and an optional built-in inertial measurement unit to correct for pose and motion effects.

21 Claims, 5 Drawing Sheets

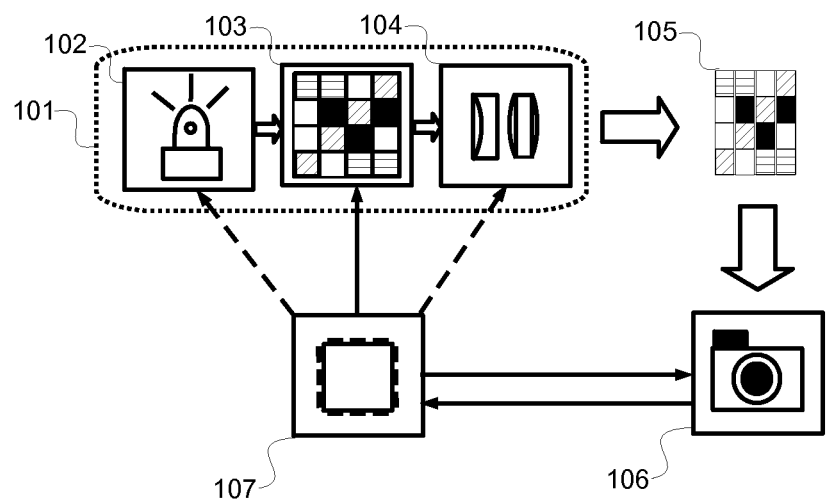
FIG. 1
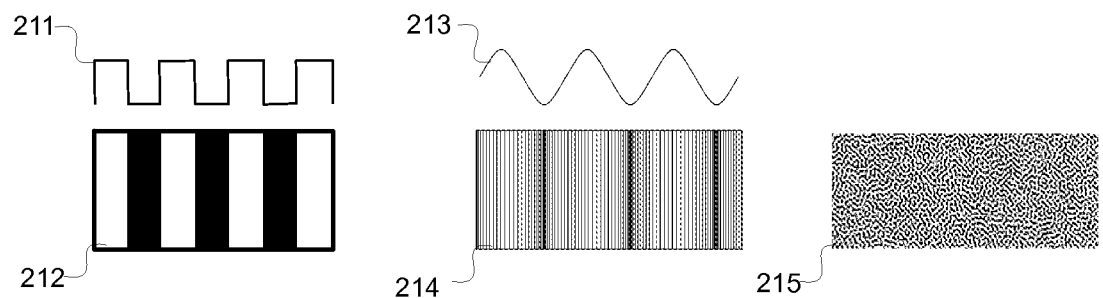
FIG. 2A  FIG. 2B  FIG. 2C

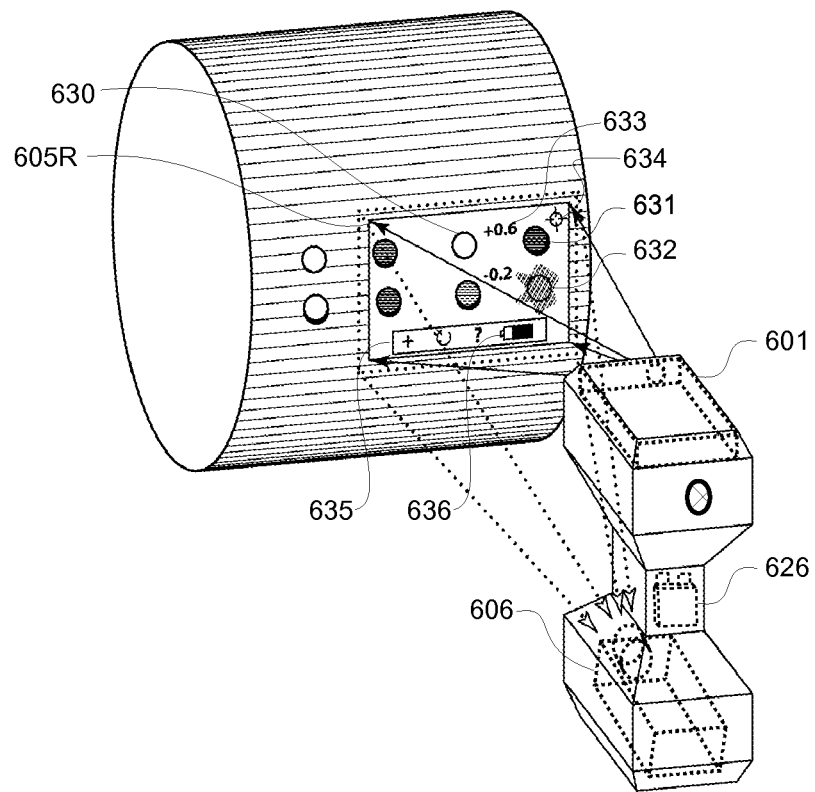
FIG. 6B
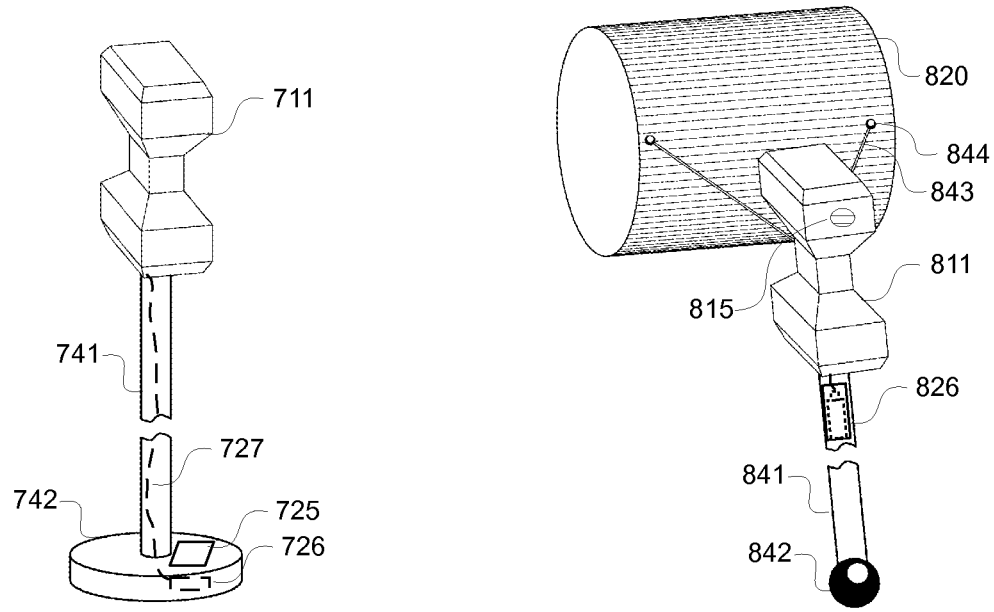
FIG. 7  FIG. 8

PORTABLE THREE-DIMENSIONAL METROLOGY WITH DATA DISPLAYED ON THE MEASURED SURFACE

RELATED APPLICATIONS

None

FEDERALLY SPONSORED RESEARCH AND DEVELOPMENT

None

APPENDICES

None

BACKGROUND

Related fields include optical measurement of surfaces by projecting structured-light patterns; projectors that project related information along with a main image; projection of images onto real objects; and real-time augmented reality.

Measurement of surface contours, textures, and discontinuous features such as pits or cracks often requires resolution on the order of microns to millimeters. Optical approaches such as laser scanning and structured-light projection are popular for their speed, non-invasiveness, and acceptable precision and accuracy. Objects routinely measured by these methods include (but are not limited to) aircraft and other vehicle bodies, precision mechanical parts, textiles, glass, sheet metal, granular substances such as abrasives and powders, and in-situ archaeological artifacts. The measurements may be part of fabrication, quality assurance and control, or forensic reconstruction of past events. Measurements of parts of the human body are applicable in a widening range of fields including security, medicine and dentistry, fabrication of prosthetics, fitting of apparel, and immersive games.

In many of these applications, quick return of measurement results is crucial to productivity, and sometimes even to human safety. A manufacturing line or medical procedure may need to be halted immediately upon discovery of an unacceptable error. Also, while some applications may use a metrology instrument in one location full-time, others may need to move the capability frequently between locations.

Many optical instruments that produce excellent measurement results in a quiet, protected laboratory are sorely challenged by the shocks, vibrations, temperature ranges and gradients, air currents, moisture, contaminants, and other variables found in factory and field environments. In these places, space is often cramped and the objects to be measured may be awkwardly positioned or in constant motion. Power outlets may be scarce, and trailing cables an unacceptable hazard. Wireless signals may be blocked or suffer from electromagnetic interference.

Typically, metrology results are displayed on a screen connected to, or integrated with, the instrument. If an operator must mark or repair problem areas on the object, looking (or in some cases walking) back and forth between the screen and the target object, or having the results communicated by a second person, consumes time and creates opportunities for mistakes. "See-through" displays, head-mounted or otherwise, alleviate some of these drawbacks. However, they may create parallax errors or obscure peripheral vision too much for safety. Also, if more than one person needs to look at the results, each of them needs a separate display or they need to take turns viewing.

These practical challenges have created a need for a 3D surface metrology instrument that displays the measurement results directly on the surface being measured. Such a display would remove ambiguity during in-situ repair work, could be viewed by several users simultaneously, and would not obscure their vision of other objects. Ideally, the instrument would be portable (e.g., compact, lightweight, and rugged), fast, accurate, versatile, and easy to use.

SUMMARY

A non-contact 3D surface metrology instrument displays the measurement results directly on a target surface being measured. A result-image generator creates, in various embodiments, false-color representations of the measurement data, local or statistical measurement values, text, pass/fail markers, fiducials, and other symbols. The projection of this image is corrected for distortions introduced by the projector and the target surface. In some embodiments, the result-image generator generates other information such as menus and instructions. Depending on the embodiment, the colors, character sizes, and layouts may be manually adjusted or may automatically adjust themselves for optimal legibility.

Embodiments of a non-contact 3D surface metrology instrument are portable, compact, lightweight, rugged, and in some cases self-contained. The same image generator and projection optics used to display the measurement results on the target surface may also project structured-light patterns for performing the measurements. The same camera used to capture measurement-pattern images may also capture projected result-images for archival. Some embodiments have few or no significantly moving parts, using liquid-crystal or microelectromechanical systems (MEMS) to generate the measurement patterns and the result-images. Light-emitting diodes (LEDs) providing the illumination are small, lightweight, durable, long-lasting, and require little or no cooling. Ruggedized lightweight instrument housings may be hand-held or mounted by various portable means. Power sources and processing electronics may be inside or outside the housing.

Embodiments of the non-contact 3D surface metrology instrument are fast, delivering essentially real-time results. Structured-light projection illuminates the entire target surface at once and eliminates the lag-time associated with scanning LCD and MEMS-based image generators can change the structured-light patterns very quickly. The camera capturing the measurement-pattern images may be electronically triggered, eliminating the delay of activating mechanical shutters. High-performance techniques such as multi-threading and graphics processing unit (GPU) computing reduce processing time.

Embodiments of the non-contact 3D surface metrology instrument are accurate. The image generators can generate Gray-code and phase-shifted measurement patterns for improved precision and robustness. For many applications, the speed alone ensures acceptably accurate measurements even for hand-held operations. Other embodiments include inertial measurement units (IMUs) to collect data on instrument pose and motion during measurement. The data from the IMU may trigger a "do-over" instruction when excessive motion results in less-than-acceptable precision or accuracy. The processor may also use IMU data to internally correct measurement data or the arrangement of result-images, to document which part of a large target surface was measured, or to combine neighboring measurements of smaller areas into a map of a larger area.

Embodiments of the non-contact 3D surface metrology instrument are versatile and easy to use. Grips and switches are ergonomic. In some embodiments, measurement triggers are configured so that activating the switch does not cause the instrument to move. Some embodiments sense external factors affecting measurement accuracy (e.g. ambient light, target size, working distance) and warn the user if the conditions are too adverse for the instrument to compensate. Embodiments with IMUs can correct the effects of some motion, warn the operator if the effects cannot be corrected, and provide horizontal text in the result-image independent of instrument pose. The colors of the result-images may be adjusted for legibility in a variety of lighting conditions, as may the size and linewidth of fiducials and characters. The camera may be configured to store result images for later archival and statistical analysis.

BRIEF DESCRIPTION OF THE DRAWINGS

FIG. 1 is a functional block diagram of a generalized metrology instrument.

FIGS. 2A, 2B, and 2C illustrate some examples of measurement patterns used in structured-light metrology.

FIG. 6B illustrates an example of a portable metrology instrument displaying a result-image on a riveted section of an aircraft body.

FIG. 7 illustrates an example of a free-standing portable metrology instrument.

FIG. 8 illustrates an example of a standing portable metrology instrument with a working-distance spacer.

DETAILED DESCRIPTION

Figure 3:
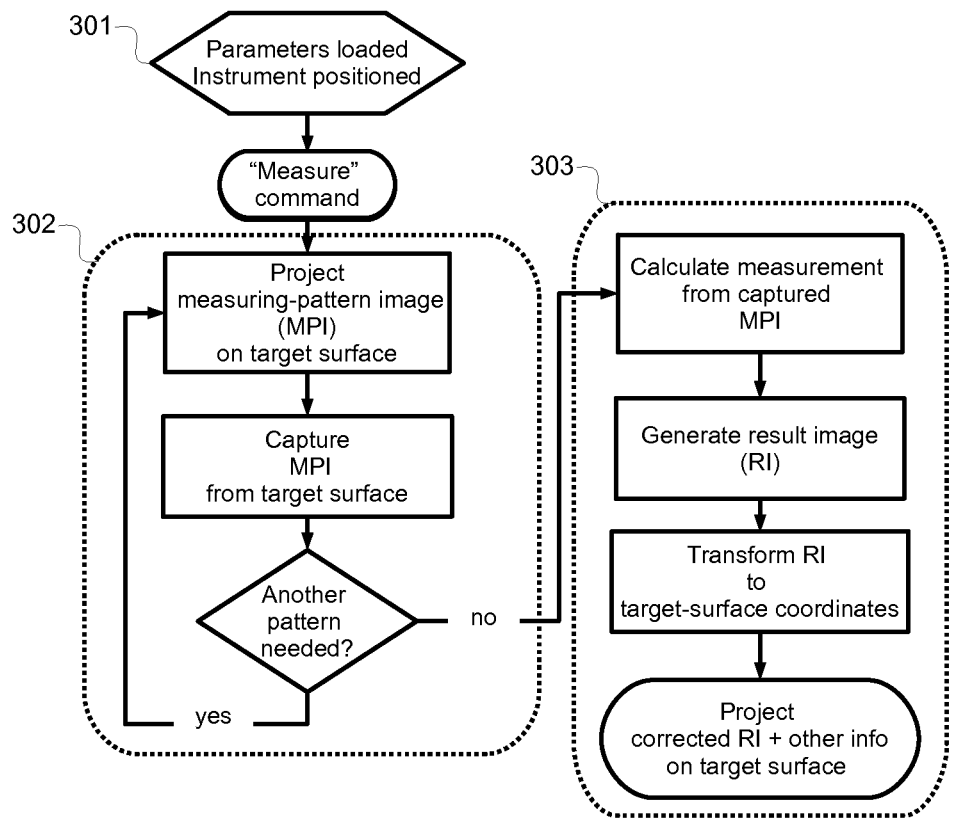
FIG. 3 is a flowchart of a generalized measurement process.

This Description will explain the operation of the basic instrument, followed by the operation of the instrument with an IMU. A walk-through of operation in a specific application will be followed by discussion of alternate embodiments.

FIG. 1 is a functional block diagram of a generalized metrology instrument. Projection assembly 101 includes, at a minimum, light source 102, image generator 103, and projection optical train 104. Image generator 103 generates images according to control signals from data processor 107. Projection assembly 101 projects an image 105 from image generator 103 on a target surface being measured. Camera 106 photographs the projected image 105 from the target surface. Camera 106 is triggered and may be otherwise controlled (e.g. autofocus; zoom; gain; baffles, stops or filters to exclude ambient light that would otherwise cause errors in the measurement data) by processor 107, and sends its captured images as measurement data to processor 107 for analysis, storage, manipulation, or rebroadcast. In some embodiments, processor 107 controls light source 102 to adjust brightness, color, pulse duty cycle, or other variables. In some embodiments, processor 107 controls focus, filtering, aperture, and optical corrections or compensations in projection optics 104.

Two types of image are projected on surfaces to be measured: a measurement-pattern image (MPI) for structured-light metrology and a result image (RI) showing some form of the measurement results and, optionally, auxiliary information and features such as fiducial marks, instructions, instrument status, menus, and other user-interface display data. In general, each MPI is projected for as brief a time as the camera's response to the projection light levels will allow, to minimize image blurring from motion of the instrument or target. The RI, if intended for direct viewing by a user, either remains "on" until turned off or its refresh frequency and duty cycle exceed the flicker fusion threshold for the brightness and color settings being used.

FIGS. 2A, 2B, and 2C illustrate some non-limiting examples of measurement patterns used in structured-light metrology. Square-wave spatial modulation 211 produces striped measurement pattern 212. Sinusoidal spatial modulation 213 produces periodic-gradient measurement pattern 214 (typically grayscale, but illustrated here with variably spaced line shading). Stochastic noise patterns such as 215 are also sometimes used. Modulation amplitude may go from "black to white" as shown, or use intermediate gray levels. Embodiments of the metrology instrument may use any suitable type of measurement pattern.

The processor compares the camera's capture of the MPI on the target surface with a stored MPI measured or modeled on a theoretical or actual reference surface. The processor derives a three-dimensional (3D) "point cloud" from the deviation between each point of the captured target MPI and the corresponding point of the stored MPI. A measurement will often include the projection, capture, and analysis of several MPIs differing in frequency, phase, orientation, structure, or any parameter where one of the patterns reveals or clarifies a surface characteristic that the other(s) might miss or obscure.

FIG. 3 is a flowchart of a generalized measurement process. Preparatory steps 301, to be completed before measuring, include calibration, setting the working distance from the instrument to the target surface, and entering or loading any other settings such as choice of measurement patterns, acquisition parameters such as brightness and ambient-light exclusion, tolerances, and visualization modes. In some embodiments, collections of these settings can be associated with a particular target type or test type and entered, edited, stored in and retrieved from the processor. After receiving a "Measure" command, the instrument executes a measure cycle 302, projecting and capturing each MPI in the set. Preferably, this is done very quickly, e.g. 12 MPIs projected and captured in 0.1 s or less. In analysis cycle 303, the processor generates the 3D point cloud for the target surface and reduces it to the results to be shown in the RI. The RI coordinates are transformed to compensate for any projector or target-surface distortion that might otherwise displace features in the RI from the corresponding part of the target surface. (For simplicity, this flowchart shows all the captures in measure cycle 302 occurring before any of the analysis of the captured images in analysis cycle 303. However, some embodiments process the already-captured MPIs in parallel with acquiring new MPIs).

Many factory, field, and operating-room environments would benefit from these 3D metrology capabilities being made portable, even hand-held. This presents challenges related to keeping the measurements precise and accurate when the instrument is not kept perfectly still. Some structured-light measurements can avoid imprecision and inaccuracy associated with instrument motion simply by operating at high speed. Others (because they require higher resolution, or longer exposure because the projected MPI is dim, or for other reasons) benefit from an added capability for the instrument to "know" how it moved during the measurement. At a minimum, it could warn the user or force a re-measurement if the motion reduced the measurement precision or accuracy below a predetermined threshold of acceptability (one of the tolerances that some embodiments allow the user to select). A more advanced embodiment can adjust the three-dimensional point cloud by removing some of the effects of the detected motion from the captured MPI sets before analyzing them. Pose and motion tracking can also enable the instrument to adapt features and locations of the result-image while it is being projected. For example, fiducials or text strings can be displayed as horizontal even when the instrument is rotated off-horizontal, or the projected features could be constrained to stay in place on the target surface even if the instrument moves or tilts while the result-image is being projected.

Inertial measurement units (IMUs), often comprising accelerometers and gyroscopes, are available in very small sizes and light weights. Coupled with a processor, they can store a history of the instrument's pose and motion as well as keeping track of its current orientation. Current orientation is useful when projecting the RI; for instance, it can enable the processor to align characters or fiducials with the external horizon even when the instrument is held in a tilted position.

Figure 4:
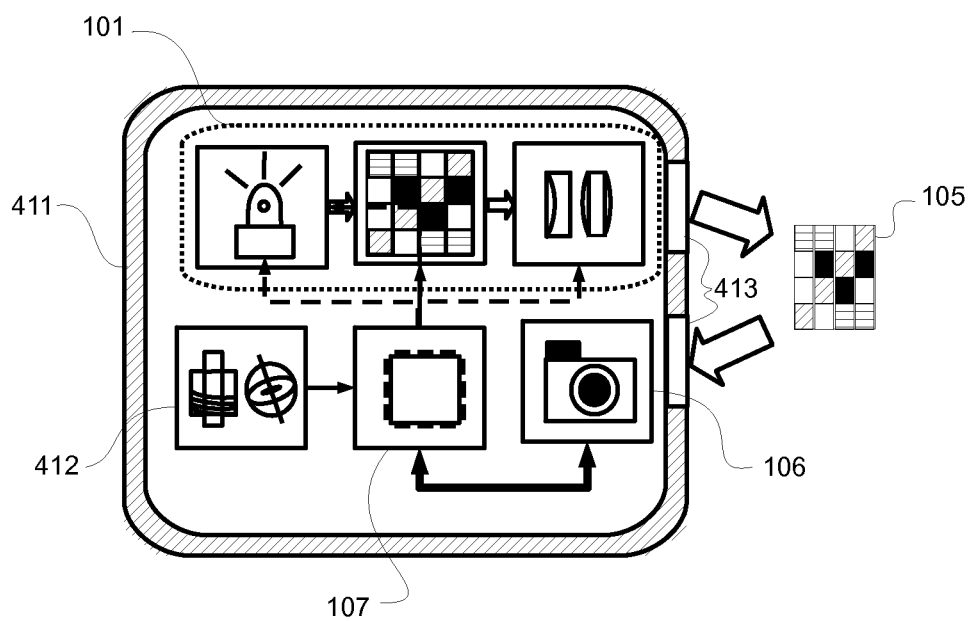
FIG. 4 is a functional block diagram of a metrology instrument including an IMU and enclosed in a portable housing.

FIG. 4 is a functional block diagram of a metrology instrument including an IMU and showing a representation of the portable housing. Here, projection assembly 101, camera 106, processor 107, and IMU 412 are enclosed in protective housing 411. Housing 411 is designed for manual transport using lightweight materials (e.g., a shell of aluminum, carbon fiber, or hard polymer) and with shock-absorbing measures (e.g., stiff metal springs or polymer foam) for projection assembly 101 and camera 106. Alternate configurations, such as that in FIG. 1 without the IMU, can also be assembled into portable housings similar to 412. Light from projection assembly 101 exits housing 411, and light from projected MPI 105 enters housing 411, through ports 413 which may or may not be fitted with windows or lenses. IMU 412 is connected to transmit measurements of instrument pose and motion to processor 107.

In a self-contained embodiment, a power source such as a battery or, for some outdoor environments, a solar cell may also be in, on, or closely connected to housing 411. Other alternatives include a data port or a wireless transmitter, receiver or transceiver for communication with an off-board processor (besides or instead of internal processor 107), or with an off-board controller.

Figure 5:
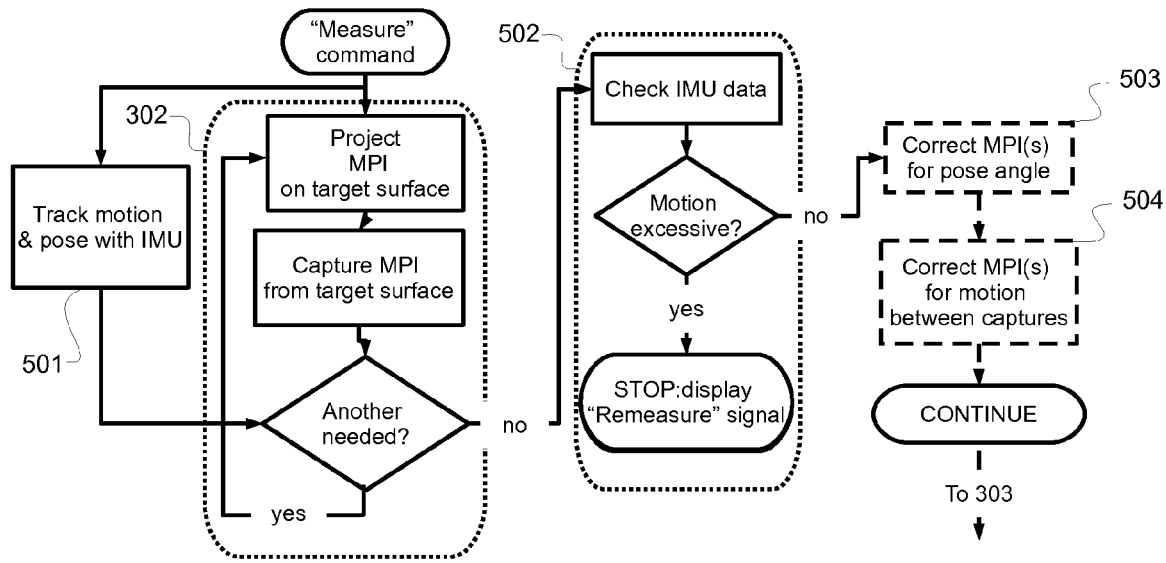
FIG. 5 is a flowchart of a measurement process using data from the IMU.

FIG. 5 is a flowchart of a measurement process using data from the IMU. Throughout measurement cycle 302, the IMU collects a pose and motion history 501 for use by the processor. Separately from (either before, as shown here, or in parallel with) analysis cycle 303, the processor performs excessive-motion check 502. Comparing the pose and motion history data with predetermined thresholds of unacceptable effects on measurement data, the system can display a warning or an instruction to re-measure the target surface if a threshold has been exceeded. Some embodiments may also use the IMU data to correct the captured MPIs for instrument pose angle, 503 (very useful if the references being compared were oriented differently). Some embodiments may also use the IMU data to offset successive MPIs to correct for motion between successive capture events.

As an instructive but non-limiting example, a workflow measuring fastener height on part of an aircraft body is described.

Figure 6A:
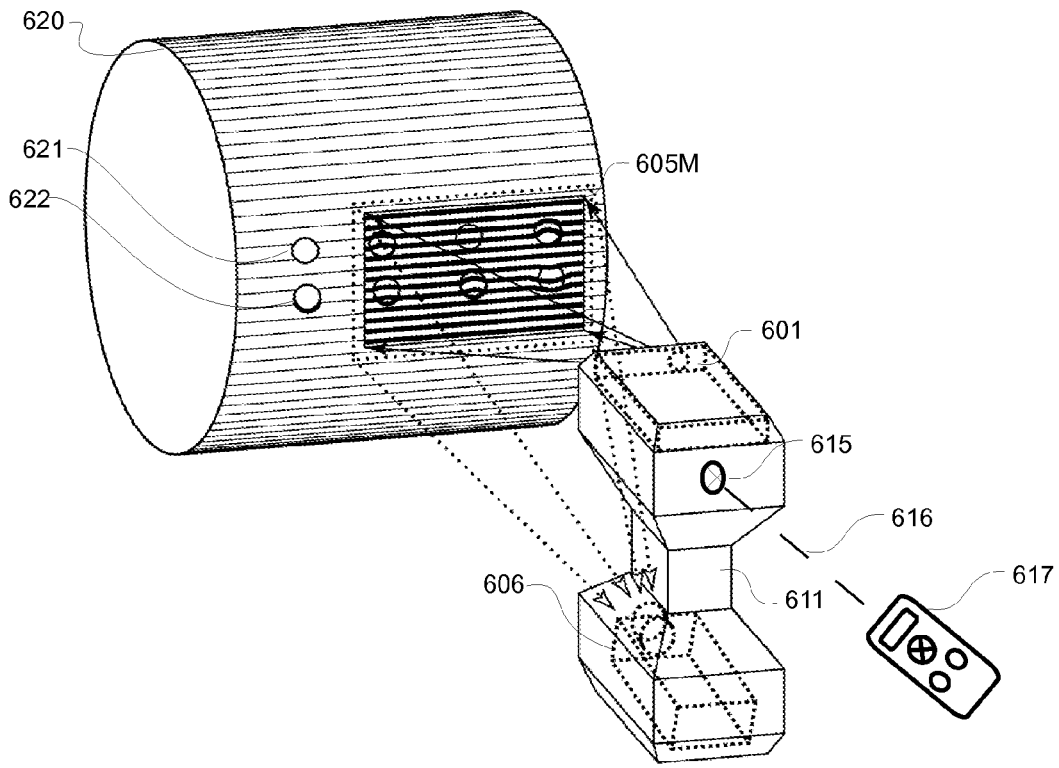
FIG. 6A illustrates an example of a portable metrology instrument measuring a riveted section of an aircraft body.

FIG. 6 illustrates an example of a portable metrology instrument measuring fasteners on a section of an aircraft body. Fasteners 621 attach body cover 620 to an underlying frame or other structure. Some fasteners 622 protrude, disturbing the air flow across body cover 620 and increasing resistance. The portable 3D metrology instrument in housing 611 projects PMI 605M from projection assembly 601. The stripes in PMI 605M are curved by the overall curve of the body and disturbed to a greater or lesser extent by the fastener heads' relief from the surface. The camera 606 captures PMI 605M for processing. Here, the field of view of camera 606 is shown as slightly larger than PMI 605M, but other embodiments could have the camera field of view slightly smaller than the PMI, or the same size, or with a small lateral offset. Substantial overlap between the fields is sufficient.

This embodiment has a wireless receiver 615 receiving a control signal 616 from a wireless remote control 617. This is one way to enable a user to send "Measure" or other commands without mechanically engaging any part of housing 611, avoiding the risk that the act of starting the measurement will cause an undesirable motion of the instrument. Control signal 616 may be radio-frequency, infrared, audio, or any other signal compatible with the work environment.

A non-limiting example of an algorithm to identify and characterize problem fasteners may run as part of the analysis cycle in the processor. After the 3D point cloud is extracted from the captured MPIs, fasteners are recognized within the point cloud using stored data on fastener sizes and shapes. For each of the found fasteners, a best-fit ellipse is calculated. A best-fit outer plane is calculated from three or more point-cloud points on a ring outside the ellipse. A best-fit inner plane is calculated from three or more point-cloud points on a ring inside the ellipse. The angle between the two planes represents the angle error of the fastener head, and the distance between the two planes at the center of the ellipse represents the relief error of the fastener head. The derived results are marked on each fastener in the result-image as a false color, grayscale, symbol, or label.

The result-image is warped (transformed into coordinates matched to projection conditions on the surface), using points stored during calibration of the projector and, in some cases, points sampled from the measurement. This ensures that result-image fastener marks land on the corresponding fasteners when the result-image is projected on the target surface.

FIG. 6B illustrates an example of a portable metrology instrument displaying a result-image (RI) of measured fasteners on an aircraft body. The measurement shown in process in the previous figure is complete, and projection assembly 601 now projects result-image 605R on the measured surface. Fastener 630 is within the predetermined tolerance and is marked differently from out-of-tolerance fasteners 631 (protrudes too far) and 632 (recessed too far, bending the surrounding surface as shown by the irregular blotch marked around it). RI 605R may also include text 633 (related to the measurements or not), fiducial 634, navigation menu 635, and status indicators such as battery-charge indicator 636 monitoring on-board battery 626.

In some embodiments, projected information such as 633-636 is automatically positioned, or adjusted in brightness or color, by the processor for best legibility on the current target surface. In some embodiments, an IMU inside the instrument keeps text 633 horizontal even if the instrument is rotated. In some embodiments, camera 606 captures result image 605R to be stored for archival, statistics, or further manipulation.

FIG. 7 illustrates an example of a free-standing portable metrology instrument. Housing 711 may be temporarily or permanently attached to monopod 741, stabilized by base 742. Optionally, some of the weight required to stabilize base 742 may be a battery pack 726 accessible through hatch 725 and connected to a power input in housing 711 by a power cable 727.

FIG. 8 illustrates an example of a standing portable metrology instrument with a working-distance spacer. Here, monopod 841 ends in a foot 842 that allows the assembly to lean toward target surface 820. A battery 826 is mounted inside monopod 841, near the top for easy access. Battery compartments inside mount legs can be implemented with any type of monopod or tripod stand; in some designs the batteries may be near the bottom of a mount leg for mechanical stability. A working-distance spacer mounted (detachably or interchangeably) to housing 811 comprises a pair of rods 843 ending in tips 844. When foot 842 rests on the floor and tips 844 rest on target surface 820, a leaning tripod is formed. Microphone 815 can receive spoken commands, another way to initiate a measurement without moving the instrument; this can be implemented on other embodiments as well.

Figure 9:
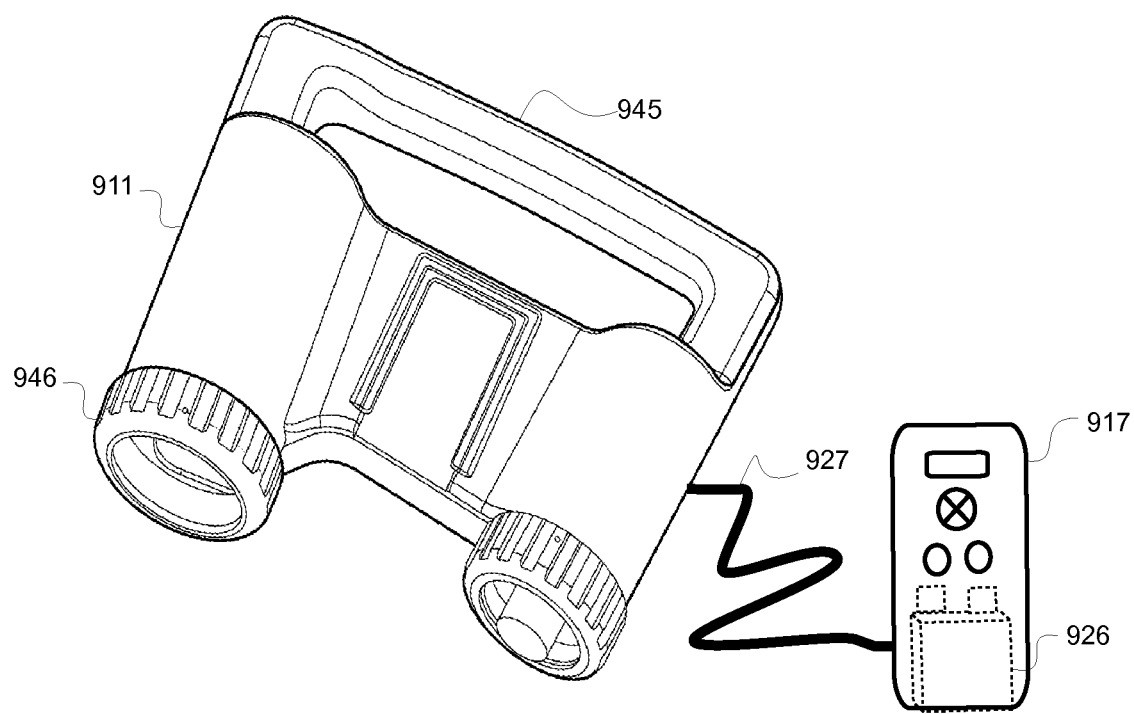
FIG. 9 illustrates an example of a hand-held portable metrology instrument.

FIG. 9 illustrates an example of a hand-held portable metrology instrument. Housing 911 may be conveniently carried, or held for measurement, by handle 945. In non-autofocus embodiments, textured focusing rings 946 may be provided for manual focusing of the camera and projection optics. In some embodiments (and with other housing types as well) a flexible cord 927 may couple the instrument to a remote control 917 to initiate measurements without jostling the instrument, a battery pack 926 to provide sufficient power without excess weight in housing 911, or a combination of both as shown here. This corded module may be, by way of non-limiting example, clipped to a belt or carried in a pocket to avoid dragging on housing 911.

Double-projector embodiments are also contemplated. Reasons for this more complex approach could include a need for continuous simultaneous measurement and result-image display (although rapid image switching in a single projector may be satisfactory in many situations) or using a non-visible measuring wavelength. In medicine, for example, tissue-penetrating near-infrared wavelengths may be used to measure features under the outermost layer of skin, and near-ultraviolet wavelengths may be used to measure surfaces where a fluorescing marker has been applied (e.g., to identify cancerous cells). Any of the mounting and holding configurations described here, as well as their equivalents, may be adapted to single- or double-projector embodiments. The projectors could be adjacent to each other or on either side of a central camera, as long as the projected fields and the camera's field of view overlap.

Those skilled in the art will recognize that many variations are possible using equivalent parts or steps to those described. The scope of patent protection for this subject matter is not limited by anything in the abstract, description, or drawings, but only by the appended claims.

I claim:

1. An apparatus for measuring a surface, the apparatus comprising:
    a portable housing,
    a projection assembly mounted in the portable housing and projecting an image on the surface,
    a camera mounted in the portable housing and configured to capture the projected image as measurement data, and
    a processor controlling the projection assembly and the camera and receiving the measurement data from the camera, where
        the projection assembly comprises an image generator, a light source, and a train of projection optics,
        the projected image comprises a measurement-pattern image or a result-image, and
        the processor derives a characteristic of the result-image by analyzing the measurement data corresponding to the measurement-pattern image.

2. The apparatus of claim 1, where the portable housing comprises at least one of a handle, a monopod, and a spacer.

3. The apparatus of claim 1, further comprising a portable power source mounted in the portable housing.

4. The apparatus of claim 1, where the processor comprises an on-board processor component mounted in the portable housing.

5. The apparatus of claim 1, where the image generator comprises one of a liquid-crystal array and a microelectromechanical system.

6. The apparatus of claim 1, where the light source has a variable spectrum controlled by the processor and comprises a light-emitting diode.

7. The apparatus of claim 1, where at least one of the light source, image generator, and train of projection optics are instrumental in projecting both the measurement-pattern image and the result-image.

8. The apparatus of claim 1, further comprising an auxiliary light source having a wavelength outside the visible spectrum.

9. The apparatus of claim 8, further comprising at least one of an auxiliary image generator compatible with the auxiliary light source and an auxiliary train of projection optics compatible with the auxiliary light source.

10. The apparatus of claim 1, where the camera is configured to exclude ambient light that would otherwise cause errors in the measurement data.

11. The apparatus of claim 1, further comprising an inertial measurement unit mounted in the portable housing and configured to transmit pose and motion data to the processor.

12. A method for measuring a surface, the method comprising:
    positioning a portable metrology instrument relative to the surface,
    projecting a measurement-pattern image from the portable metrology instrument onto the surface,
    capturing as measurement data a captured image of the measurement-pattern image projected on the surface,
    creating a point cloud model representing the surface, in which a point in the point cloud model is based on comparing a point in the measurement data with a corresponding point in a stored version of the measurement-pattern image,
    creating a result-image from the point cloud and from stored information, transforming the result-image into coordinates matched to projection conditions on the surface, and
    projecting the result-image onto the surface from the portable metrology instrument.

13. The method of claim 12, where the result-image is projected within 0.1 second after the measurement image.

14. The method of claim 12, where the result-image comprises at least one of a false-color representation of the measurement, a summary of results of the measurement, a symbol dependent on the measurement, an alphanumeric character, a navigational symbol, a status indicator, a menu, and an instruction.

15. The method of claim 12, further comprising monitoring the pose and motion of the portable metrology instrument and doing at least one of:
    issuing a warning if the portable metrology instrument moved in excess of a predetermined threshold during the projecting and capturing of the measurement-pattern image, storing the location and orientation of an area of the surface being measured, adjusting the point cloud to compensate for the pose and motion of the portable metrology instrument during the projecting and capturing of the measurement-pattern image, and adapting a feature location and orientation in the result-image to compensate for the pose and motion of the portable metrology instrument during the projecting of the result-image.

16. The method of claim 12, further comprising recording the result-image as projected on the surface.

17. The method of claim 12, further comprising adjusting at least one of color, brightness, and feature position in the result-image to optimize visibility or legibility of the result-image, where the adjusting is partially responsive to a characteristic of the measurement data.

18. A non-transitory machine-readable storage medium programmed with data and instructions, the data and instructions comprising:

reference data, user-interface display data, and instructions for generating a structured-light pattern, projecting the structured-light pattern on a surface to produce a measurement-pattern image, capturing the measurement-pattern image as measurement data, recording a pose-and-motion history affecting the measurement data, analyzing the measurement data with the reference data and the pose-and-motion history to produce a measurement result, generating a result-image from the measurement result and the user-interface display data, transforming the result-image into surface-projection coordinates to produce a corrected result-image, and projecting the corrected result-image onto the surface.

19. An apparatus for measuring a surface, the apparatus comprising:

a portable housing, a projection assembly mounted in the portable housing and projecting an image on the surface, wherein the projection assembly comprises an image generator, a light source, and a train of projection optics, a camera mounted in the portable housing and configured to capture the image as measurement data, wherein the image comprises a measurement-pattern image or a result-image, wherein the camera is further configured to capture gestures, and a processor controlling the projection assembly and the camera and receiving the measurement data from the camera, wherein the processor derives a characteristic of the result-image by analyzing the measurement data corresponding to the measurement-pattern image, wherein the processor is configured to interpret the gestures captured by the camera and execute commands based on the interpreted gestures.

20. The apparatus of claim 19, wherein the projection assembly is configured to project control images for interaction with a user.

21. An apparatus for measuring a surface, the apparatus comprising:

a portable housing, a projection assembly mounted in the portable housing and projecting an image on the surface, wherein the projection assembly comprises an image generator, a light source, and a train of projection optics, a camera mounted in the portable housing and configured to capture the image as measurement data, wherein the image comprises a measurement-pattern image or result-image, an gesture recognition device configured to capture and interpret gestures, and a processor controlling the projection assembly and the camera and receiving the measurement data from the camera, wherein the processor derives a characteristic of the result-image by analyzing the data corresponding to the measurement-pattern image, wherein the processor is configured to execute commands received from the gesture recognition device.

* * * * *